US012589232B2

(12) United States Patent
Weber et al.

(10) Patent No.: US 12,589,232 B2
(45) Date of Patent: Mar. 31, 2026

(54) MEDICAL CONNECTOR WITH AUTOMATIC SEALING ON DISCONNECTION

(71) Applicant: Fresenius Medical Care Deutschland GmbH, Bad Homburg (DE)

(72) Inventors: Tobias Weber, St. Wendel (DE); Robert Berlich, St. Wendel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1051 days.

(21) Appl. No.: 17/639,940

(22) PCT Filed: Sep. 1, 2020

(86) PCT No.: PCT/EP2020/074284
§ 371 (c)(1),
(2) Date: Mar. 3, 2022

(87) PCT Pub. No.: WO2021/043737
PCT Pub. Date: Mar. 11, 2021

(65) Prior Publication Data
US 2022/0339423 A1      Oct. 27, 2022

(30) Foreign Application Priority Data
Sep. 5, 2019    (DE) ..................... 10 2019 123 806.4

(51) Int. Cl.
*A61M 39/18*        (2006.01)
*A61M 39/16*        (2006.01)
*A61M 39/26*        (2006.01)

(52) U.S. Cl.
CPC .......... *A61M 39/18* (2013.01); *A61M 39/165* (2013.01); *A61M 39/26* (2013.01)

(58) Field of Classification Search
CPC .... A61M 39/18; A61M 39/165; A61M 39/26; A61M 39/12; A61M 39/20; A61M 39/10;
(Continued)

(56) References Cited

U.S. PATENT DOCUMENTS 5,204,652 A *  4/1993  Baker ................. F16K 31/0655
                                                    335/238
2005/0197646 A1    9/2005  Connell et al.
(Continued)

FOREIGN PATENT DOCUMENTS

CN          102131542 A      7/2011
CN          107029344 A      8/2017
(Continued)

OTHER PUBLICATIONS

Taiwanese Office Acton.
(Continued)

*Primary Examiner* — Chelsea E Stinson
*Assistant Examiner* — Anh Bui
(74) *Attorney, Agent, or Firm* — Kilyk & Bowersox, P.L.L.C.

(57)                    ABSTRACT
The present invention relates to a medical connector with automatic sealing on disconnection and to a method of connecting/disconnecting a medical connector.

9 Claims, 15 Drawing Sheets

Figure 1:
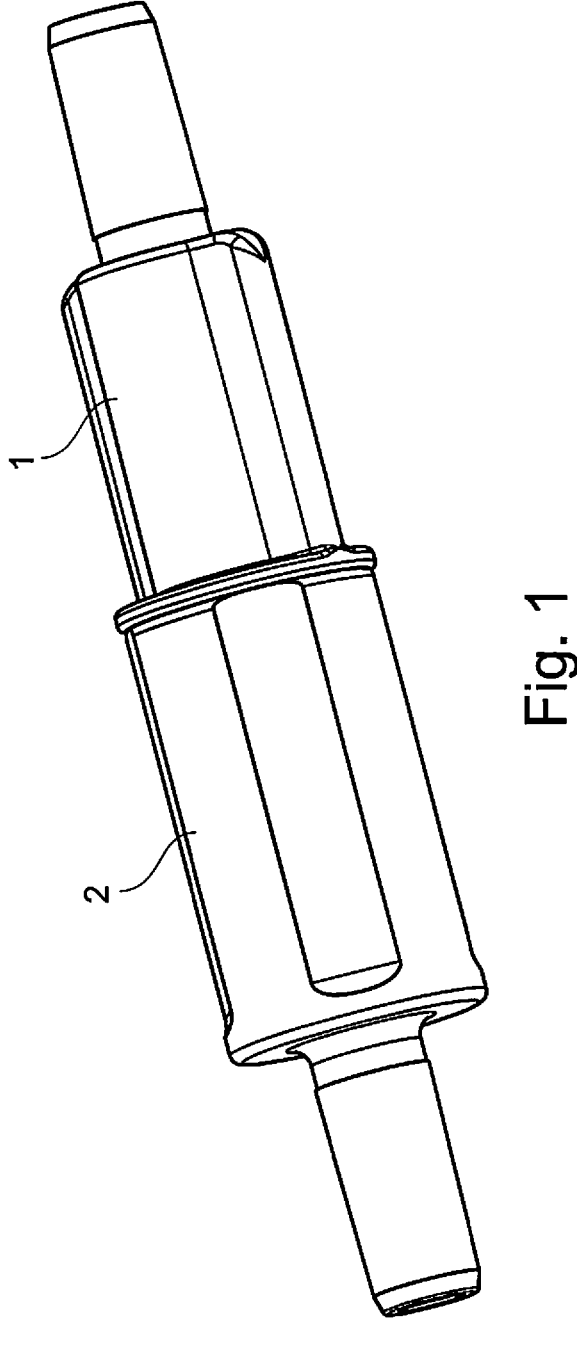

(58) Field of Classification Search
CPC .... A61M 2039/268; A61M 2039/1033; A61M
1/28; F16B 33/02; F16L 15/002; E12B
17/0423
See application file for complete search history.

(56) References Cited

U.S. PATENT DOCUMENTS

| | | | | |
|---|---|---|---|---|
| 2007/0017583 | A1* | 1/2007 | Fangrow, Jr. ......... | A61M 39/26 |
| | | | | 137/614.06 |
| 2007/0088351 | A1 | 4/2007 | Ewaschuk et al. | |
| 2011/0015580 | A1 | 1/2011 | Stroup | |
| 2012/0209168 | A1 | 8/2012 | Katsuyoshi | |
| 2021/0009335 | A1* | 1/2021 | Wilshinsky ......... | A47J 31/4407 |

FOREIGN PATENT DOCUMENTS

| | | |
|---|---|---|
| EP | 2 138 202 | 12/2009 |
| EP | 2 440 280 | 4/2012 |
| JP | 08215311 A | 8/1996 |
| JP | 11253553 A | 9/1999 |
| JP | 11319078 A | 11/1999 |
| JP | 2003210574 A | 7/2003 |
| KR | 10-2007-0095983 A | 10/2007 |
| KR | 1020170013407 | 2/2017 |
| WO | WO 2010/142385 | 12/2010 |
| WO | WO 2014/210418 | 12/2014 |

OTHER PUBLICATIONS

Japanese Office Action.
Office Action issued in corresponding Korean Patent Application No. 10-2022-7010983 dispatched Nov. 25, 2025 (8 pages).

* cited by examiner

MEDICAL CONNECTOR WITH AUTOMATIC SEALING ON DISCONNECTION

The present invention relates to a medical connector with automatic sealing on disconnection and to a method of connecting and disconnecting a medical connector.

Various fluid connections are required in the medical sector, inter alia in intense care units in hospitals, to supply patients with a plurality of fluids, for example infusion solutions, replacement solutions, dialysis solutions, liquid medication, or nutrient solutions. In addition, different treatment systems or treatment apparatus also have to be fluidically connected to one another via suitable connectors.

The disadvantage of all of these connections is that the fixed-position unit (at the machine or at the patient) has to be manually closed again after connection of a fresh sterile product. This is an indispensable step since the connection is otherwise open to the environment and could be contaminated.

Since this part is not replaced by a fresh, sterile part, but rather remains at the machine or at the patient, the risk of microbial growth after contamination is particularly high.

A typical application is that a fixed access port is as a rule already applied to the patient on admission to the hospital. This access port is opened for the supply of fluid medical solutions in that a closure cap is removed and a corresponding fluid connection is then established. A typical, standardized type of connection is the Luer connection.

After the end of the supply of the medical solution, the patient access port is closed again in that the closure cap is screwed back onto it again.

The patient access port (vascular access port, peritoneal access port, etc.) remains at the body here and germs that were transferred via the air or via a direct contact can multiply if a sterile closure is not reestablished. Contamination/infection of the patient access port can hereby occur since germs may have been able to settle at the closure cap and can move on into the blood circulation, the abdomen, the gastrointestinal tract, or into body tissues of the patient.

This problem can be minimized in that sterile closure caps are used or also caps saturated in disinfectants (iodide, alcohol, etc. (example from 3M). However, minimal amounts of the disinfectant may enter in this process. In addition, it results in a corresponding additional effort in material and sterilization processes. And it also has to be ensured from an organizational aspect that such a sterile closure cap is always present when needed.

It can, however, also be the access port to a machine and/or to a disposable which remains in or at a machine for a longer time period and which should be tightly closed between treatments or treatment steps.

The medical connector is therefore particularly exceptionally suitable for hemodialysis, peritoneal dialysis, and for continuous ambulant peritoneal dialysis (CAPD).

The continuous ensuring of the sterility on the connection/disconnection of a patient access port is in particular essential in peritoneal dialysis (PD) since a patient is connected to or disconnected from sterile solution bags manually or via a corresponding treatment machine up to four times a day over several years.

There is additionally the problem with peritoneal dialysis that the immune defense is relatively low in the peritoneal area and the likelihood of peritonitis in the case of a contamination with germs is very high and serious consequences up to a loss of the dialyzing function of the peritoneum can occur.

For these reasons, closure caps are typically used after the administration of the peritoneal dialysis solution as part of peritoneal dialysis that have been soaked with iodide and that should ensure a sterility of the closure cap and of the patient access port as best as possible for the duration of the remaining of the PD solution in the abdomen. However, small amounts of disinfectant can also enter into the peritoneal space in this process.

Alternatively to this, a connector can also be used that automatically closes the patient access port on disconnection. In this respect, the progress of the treatment, in particular the administration of fresh dialysis solution and the drainage of consumed/used dialyzate is also controlled via the connector. It is, however, disadvantageous with this solution that a complicated mechanical structure is required for it that is relatively large and bulky and is additionally cost-intensive.

It is thus the underlying object of the present invention to alleviate or remedy the disadvantages known from the prior art. It is specifically an object of the present invention to provide a simple medical connector that reduces the risk of contamination with germs in a patient access port.

This object is achieved by a connector in accordance with the invention having a first connector part and a second connector part. The present invention furthermore relates to a method for a germ-reduced connection/disconnection of a medical connector.

Handling on connection/disconnection procedures is substantially simplified due to the advantageous design of the connector. It is furthermore ensured that the fluid connection is closed by a fresh sealing pin on every disconnection.

A medical connector in accordance with the present invention has a first connector part having an elongate base body with a lumen for conducting a fluid, having a first threaded portion that is arranged at an outer side of the base body and that enables a releasable connection of the first connector part to a correspondingly matched second connector part, and having a second threaded portion that is arranged at the lumen side at an inner side of the base body and that enables a releasable connection of the first connector part to a correspondingly matched sealing pin. The thread pitch of the first threaded portion differs from the thread pitch of the second threaded portion here.

The thread pitch of the second threaded portion is preferably larger than that of the first thread pitch. It can, however, also be a multiple of the thread pitch of the first threaded portion. The second threaded portion is preferably larger than the first.

It has furthermore been found to be advantageous if a blocking element or a sealing pin that has a lumen is arranged in the lumen of the first connector part so that fluid can flow through the sealing pin and the lumen of the elongate base body of the first connector part. It is also conceivable and covered by the invention that the sealing pin is alternatively or additionally flowed around by fluid. A flowing through and/or a flowing around is/are thus conceivable.

The sealing pin can adopt an open position in which a fluid can flow through the lumen of the connector and of the sealing pin and can thus be supplied to a patient. The sealing pin can additionally adopt a blocking/closed position in which the sealing pin blocks a fluid flow through the connector and thus, for example, seals a patient access port in a fluid-tight manner and thus seals against germs and against the entry of optional disinfectants.

At its outer side, the sealing pin preferably has a threaded portion that is adapted to enter into threaded engagement with the second threaded portion of the first connector.

Provision can be made in an alternative embodiment that the sealing pin does not have a lumen and that the fluid can flow past the sealing pin.

The sealing pin furthermore preferably has a bounding element, preferably in the form of a toothed block, that restricts a rotation of the sealing pin relative to the first connector part and/or relative to the connector/to a second connector part to one direction.

It has furthermore proved to be advantageous in practice if the sealing pin preferably has a fixing element at the end opposite the bounding means, by means of which fixing element the sealing pin can be releasably or non-releasably fixed to a closure element, preferably via a latched connection and/or via an undercut. The sealing pin can, for example, be held at a closure cap of a patient access port by means of the fixing element.

A connector in accordance with the invention furthermore preferably has a second connector part having an elongate base body with a lumen for conducting a fluid, and having a reception section preferably concentrically surrounding the lumen to receive a first threaded portion arranged at the outer side of the base body of a first connector part. The receiving section of the second connector part has a threaded portion that is adapted to enter into threaded engagement with the first threaded portion of the first connector part.

A bounding element, preferably in the form of a toothed block, is preferably provided at an inner side of the lumen of the second connector part at the lumen side and is adapted to cooperate with a corresponding bounding element of a sealing pin to restrict a rotation of the sealing pin to one direction.

The boundary element is preferably formed as a plurality of ribs that extend axially along the elongate base body and along which a sealing pin received in the second connector part is preferably axially displaceable.

A sealing pin that has a lumen is preferably arranged in the lumen of the second connector part so that fluid can flow through the sealing pin and the lumen of the elongate base body of the second connector part to the patient, for example.

A connector in accordance with the invention preferably has a first connector part and a second connector part, with the first connector part preferably being releasably connected to the second connector part by means of a threaded engagement.

It has furthermore proven to be advantageous if a sealing pin is arranged in a common lumen formed by the lumens of the first and second connector parts. The sealing in is in this respect preferably movable by a relative movement of the first connector part to the second connector part between an open position in which the sealing pin enables a fluid flow through the common lumen and a closed position in which the sealing pin blocks the fluid flow through the common lumen.

In a further alternative embodiment, the flow rate or flow amount can be regulated or controlled by a displacement of the sealing pin.

Another aspect of the invention relates to a method of fluidically connecting and/or disconnecting a medical connector, said method comprising the steps:

Releasably connecting a first connector part to a second connector part, preferably by screwing the first threaded portion of the first connector part onto the first threaded portion of the second connector part. The first connector part here has a sealing pin that is arranged in the lumen of the first connector part so that a common lumen for conducting fluid is formed by the first connector part, the second connector part, and the lumen of the sealing pin. In this arrangement, the first connector part can, for example, be arranged at a supply line and the second connector part can be arranged at a patient access port. Fluid can thus be supplied to the patient by the supply line.

After the end of the supply of fluid to the patient, a release of the first connector part from the second connector part takes place by a relative movement, e.g. a rotational movement, of the first connector part relative to the second connector part, whereby the sealing pin is moved into a closed position and remains in the second connector part when the first connector part is released from the second connector part. An interaction of the bounding elements of the second connector part and of the sealing pin prevents the sealing pin from arbitrarily rotating along with the rotation of the first connector part.

The pin would not move into the closure position due to the co-rotation. The protective cap, not the toothed block, ensures the remaining in the closure position.

The pin is thereby pushed into the closure position. In the closed position, the sealing pin remains in the lumen of the second connector part. The lumen of the second connector part is thus screened from germs and/or disinfectant penetrating from the outside.

A releasable connection of a closure element, in particular in the form of a closure cap, to the second connector part can thereupon take place. A closure cap is, for example, screwed onto the patient access port. The sealing pin is pressed into the lumen of the second connector part in the axial direction by the movement of the closure cap relative to the second connector part, whereby the lumen of the second connector part is sealed to the outside in a fluid tight manner. The closure cap furthermore prevents the pin from being able to move out of its closure position again, e.g. due to vibrations.

This step is optional. The case is also conceivable and covered by the invention that the forward movement of the pin ends with the rotational movement and moves to "stop". The cap then only snaps in. The further forward movement of the pin into the patient/machine connector is a safety feature to lock the pin at a deeper position.

The sealing pin is preferably fixed to the closure element by means of the fixing element of the sealing pin on the connecting of the closure element to the second connector part. This embodiment has the advantage that on a subsequent removal of the closure element for a renewed connection of the second connector part (e.g. patient connection), the sealing pin is removed simultaneously with the closure element, whereby the lumen of the second connector part is fluidically opened. The fixing of the sealing pin to the closure element preferably takes place via a latch connection and/or via an undercut at a corresponding receiver of the closure element. The sealing pin is thus preferably held at the closure element by means of shape matching.

A release of the closure element from the second connector part thereupon takes place, wherein, at the same time as the release of the closure element, the sealing pin connected thereto is also released from the second connector part, whereby the lumen of the second connector part is fluidically opened and can again be connected to a supply line.

The connector in accordance with the invention furthermore ensures that a new sealing pin is provided for every treatment, whereby the risk of contamination can be considerably reduced.

Further advantages, features, and effects of the present invention result from the following description of preferred embodiments and with reference to the Figures. Components that are the same or similar are marked with the same reference numerals in the Figures.

Figure 2A:
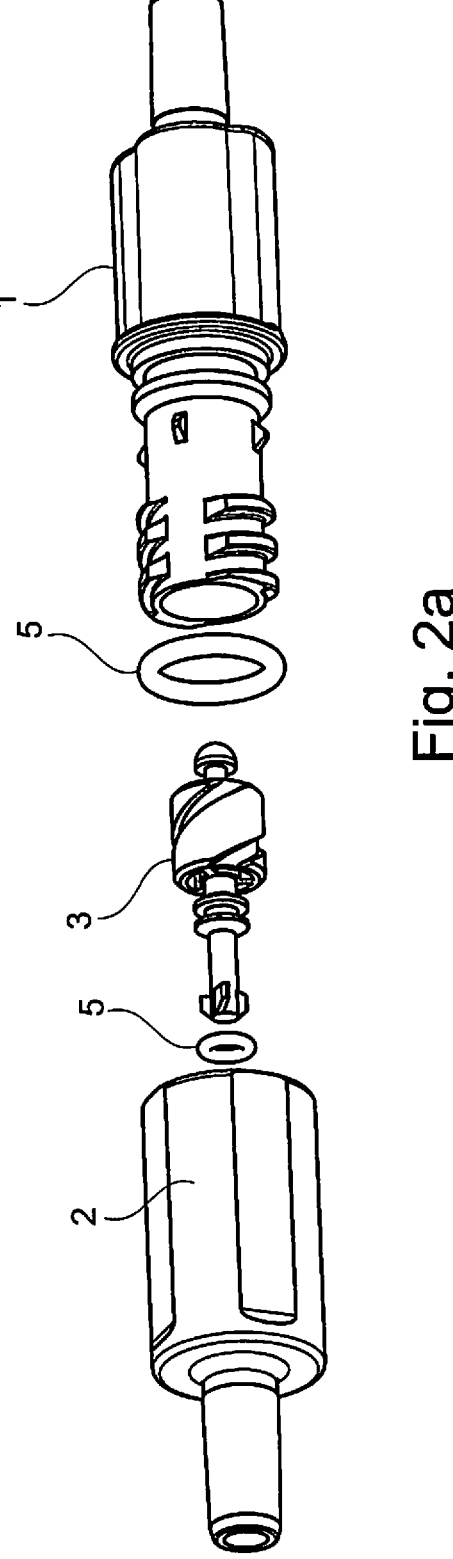
Figure 3A:
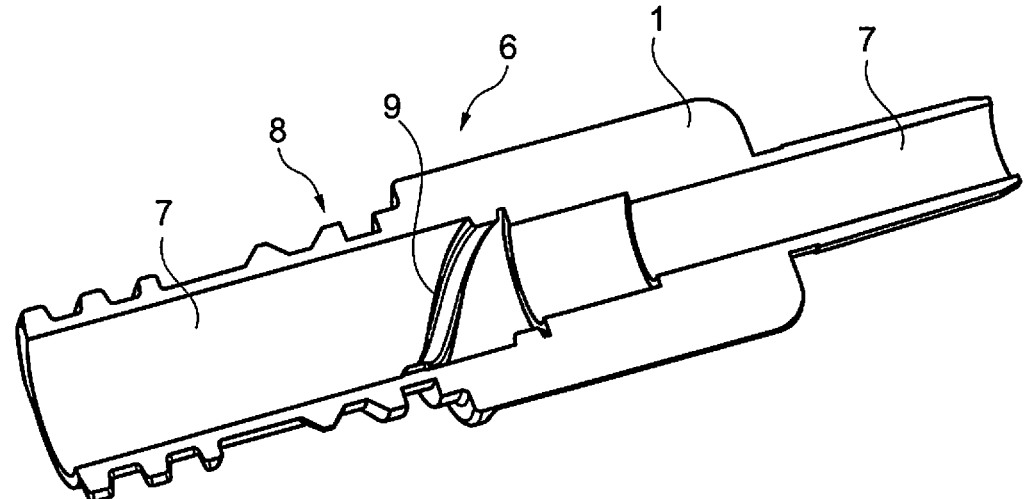
Figure 4A:
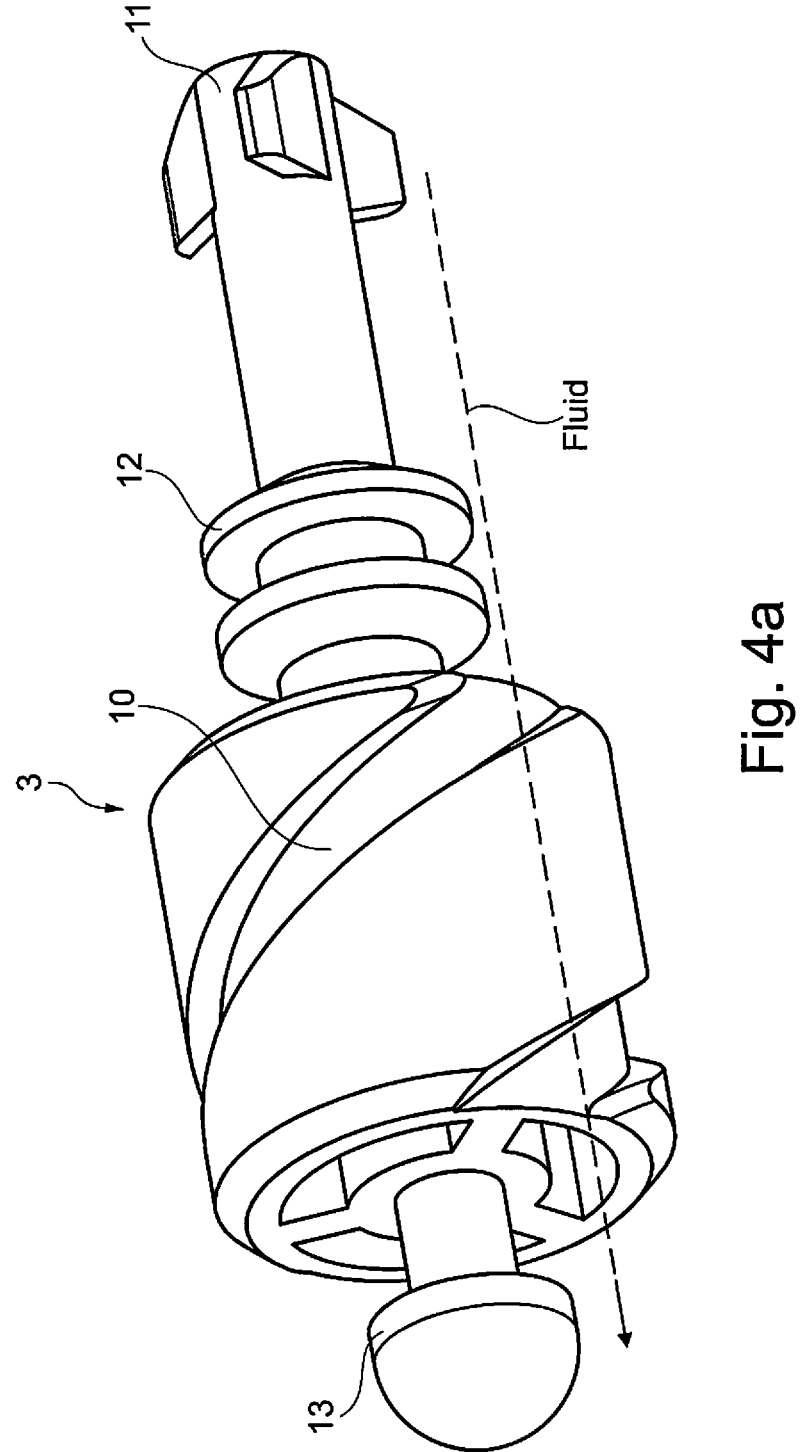

There are shown:

FIG. 1: a connector in accordance with the invention with first and second connector parts;

FIGS. 2*a, b*: an exploded representation of the connector of FIG. 1 and a closure cap;

FIGS. 3*a, b*: a sectional view of the first connector part;

FIGS. 4*a, b, c*: a sealing pin

Figure 5:
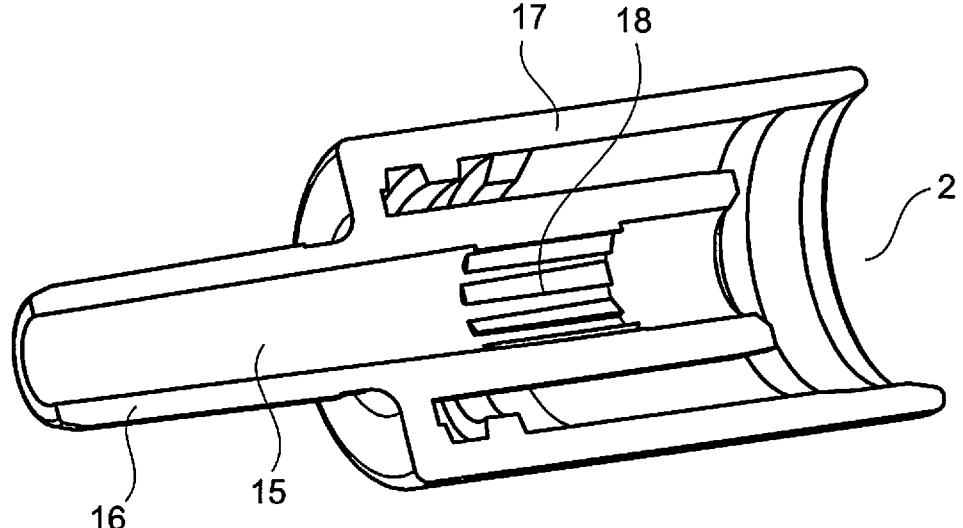
Figure 6:
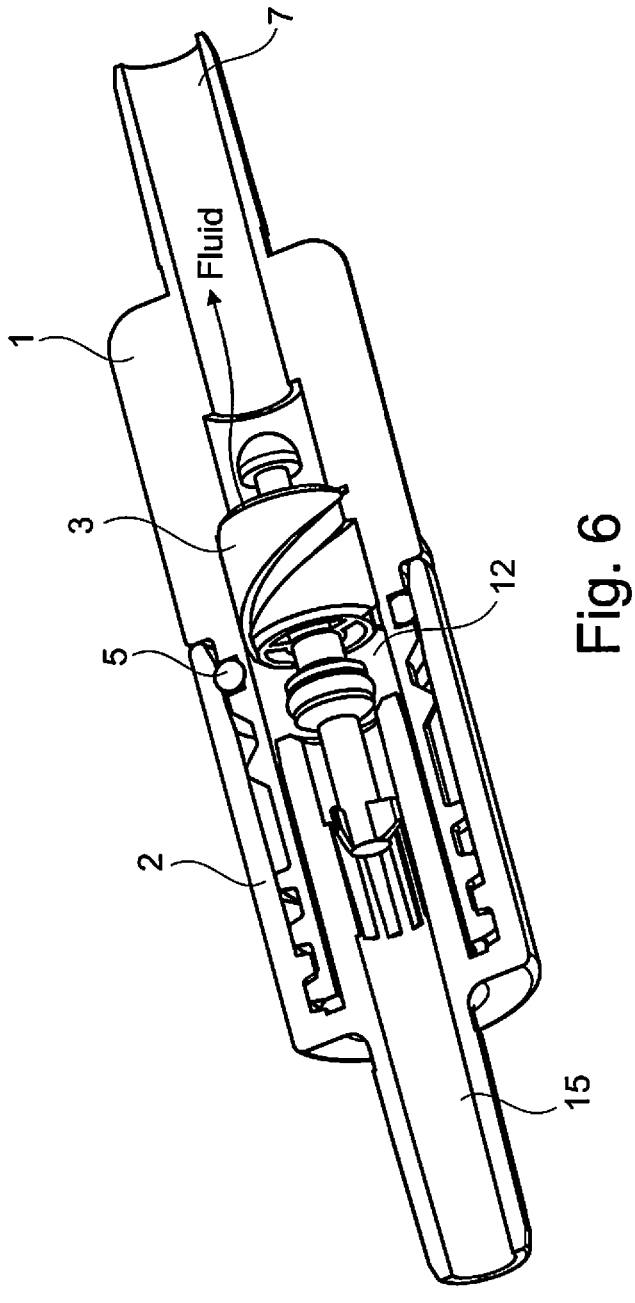
Figure 7A:
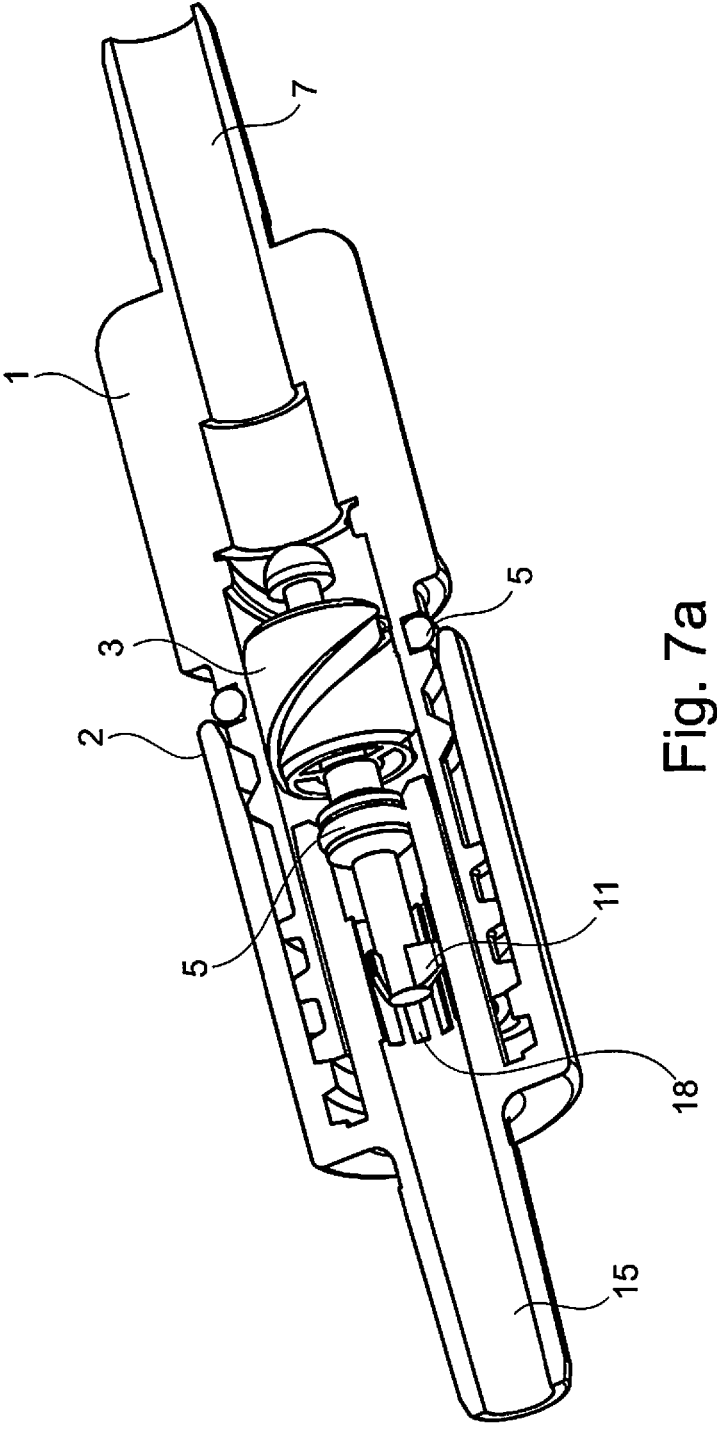
Figure 8A:
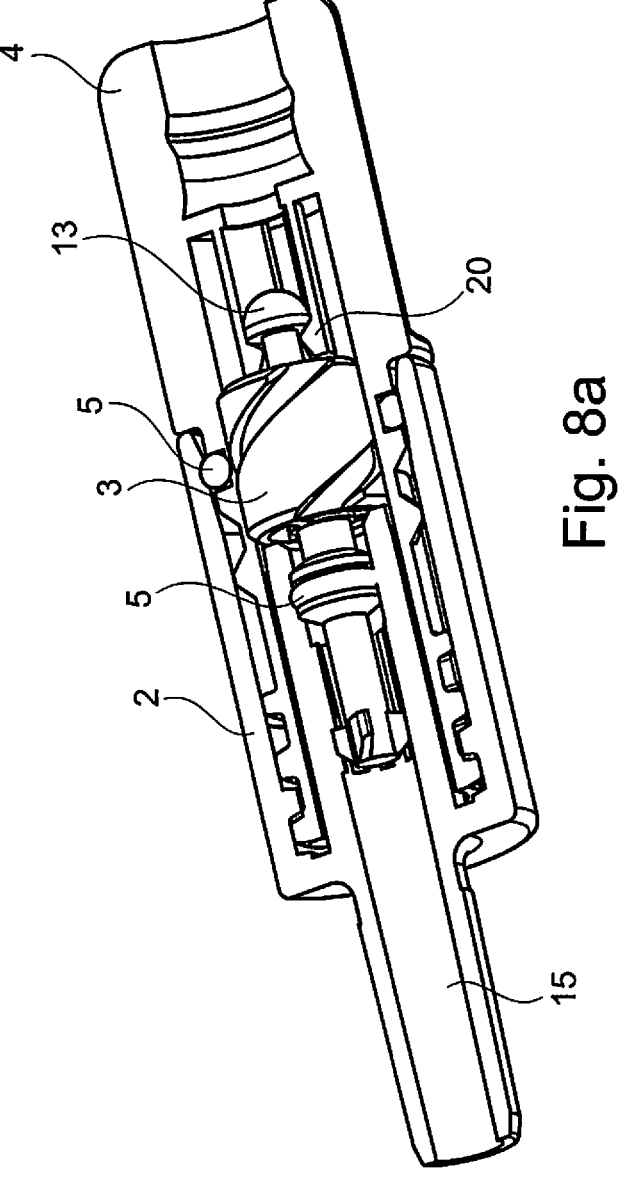
Figure 9:
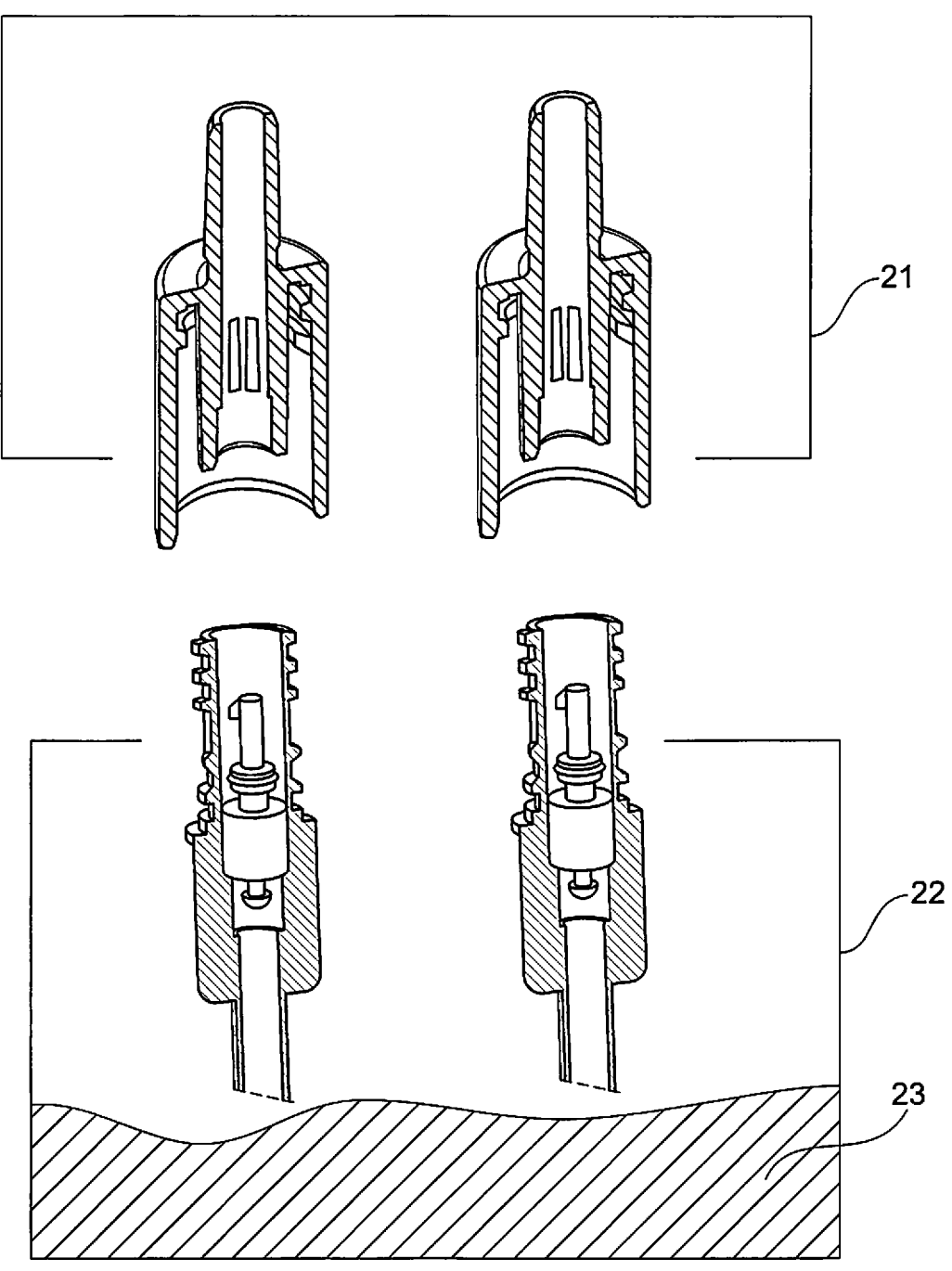

FIG. 5: a sectional view of the second connector part;

FIG. 6: a sectional view of a connector in accordance with the invention in which the sealing pin is in the open position;

FIGS. 7*a, b*: a sectional view of a connector in accordance with the invention on disconnection;

FIGS. 8*a, b*: a sectional view of a second connector part with a screwed on closure cap and a removal of the sealing pin with the closure cap; and FIG. 9: a schematic view of second connectors in accordance with the invention between an extracorporeal blood treatment apparatus and a disposable article.

FIG. 1 shows a connector in accordance with the invention having a first connector part 1 and a second connector part 2 that are releasably connected/screwed to one another.

Figure 2B:
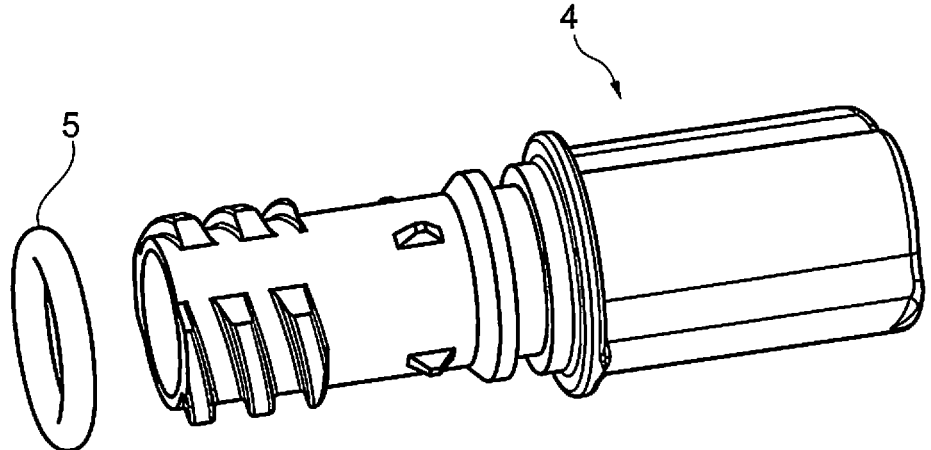

As shown in FIG. 2, the connector in accordance with the invention comprises a sealing pin 3 that is arranged in a common lumen of the first and second connector parts 1, 2. In addition, a closure element in the form of a closure cap 4 is shown in FIG. 2 that can be screwed onto the second connector part instead of the first connector part. The intermediate spaces between the sealing pin 3 and the first and second connector parts 1, 2 are sealed in a fluid-tight manner by means of sealing elements, e.g. in the form of O rings 5.

Figure 3B:
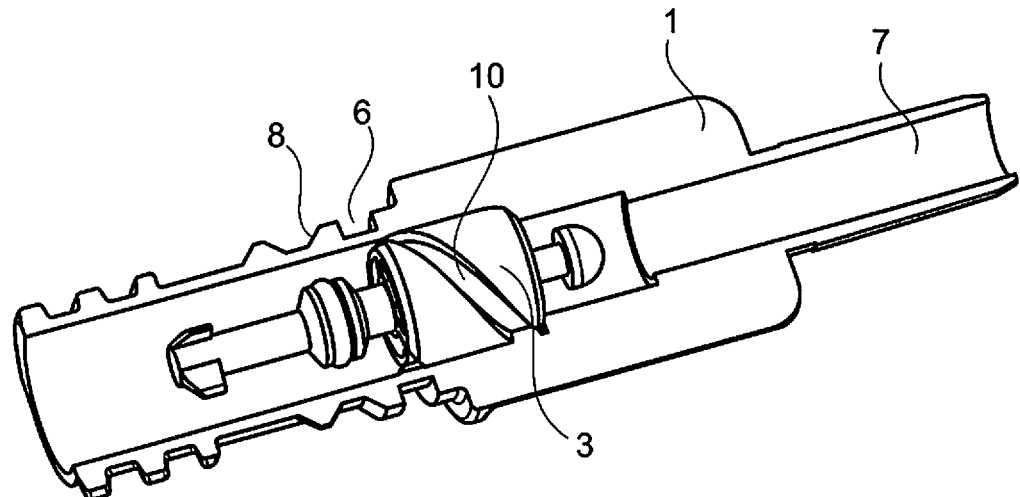

As shown in FIG. 3, the first connector part has an elongate base body 6 with a lumen 7 for conducting a fluid. A first threaded portion 8 that enables a releasable connection of the first connector part 1 to a correspondingly matched second connector part 2 is arranged at an outer side of the base body 6. A second threaded portion 9 that enables a releasable connection of the first connector part 1 to a correspondingly matched sealing pin 3 that has a corresponding threaded portion 10 is arranged at an inner side of the base body 6 at the lumen side. The thread pitch of the first threaded portion 7 differs from the thread pitch of the second threaded portion 9. The threaded portion 9 preferably has twice the thread pitch in comparison with the threaded portion 7.

Figure 4B:
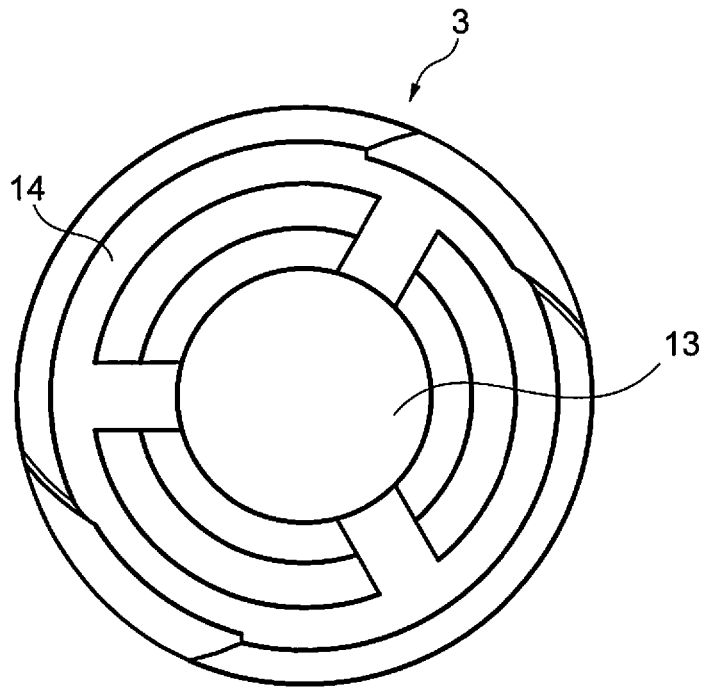
Figure 4C:
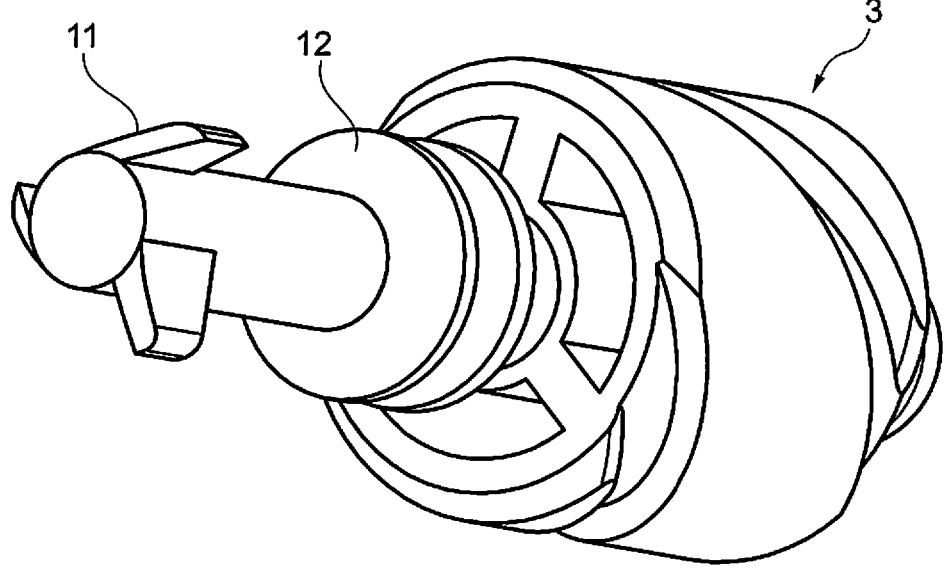

FIG. 4 shows a sealing pin in detail. FIG. 4*b* shows a side view of the sealing pin 3. The peripheral threaded portion 10 is easily visible in FIG. 4. The sealing pin has a bounding element in the form of a toothed block 11 at a first axial end (at the right in FIG. 4*a*). The sealing pin 3 furthermore has a sealing section 12 that consists, for example, of two peripheral projections between which an O ring can be arranged. The sealing pin 3 is formed as hollow in its interior or comprises at least one lumen so that fluid, as indicated by an arrow in FIG. 4*a*, can flow through the lumen of the sealing pin 3.

At the other axial end (at the left in FIG. 4*a*), the sealing pin 3 has a fixing element that has the shape of a latching button 13 in this embodiment. The latching button 13 can be introduced into a corresponding receiver of a closure cap 4 and can latch therewith so that the sealing pin 3 is held securely at the closure cap 4.

FIG. 4*b* shows a view of the sealing pin 3 from the left side in FIG. 4*a*. The lumens 14 of the sealing pin 3 are clearly recognizable in this representation. The toothed block 11 is particularly easily recognizable in FIG. 4*c*.

FIG. 5 shows a second connector part 2 of a connector in accordance with the invention. The second connector part preferably has a set-back inner dome. Such a connector part 2 can, for example, be provided at a patient access port. The second connector part 2 comprises an inner lumen 15 for conducting fluid that is defined by an inner sleeve 16. The second connector part additionally comprises an outer sleeve 17. A bounding element in the form of a plurality of axial ribs and/or cutouts 18 is arranged at the surface of the inner sleeve 16 at the lumen side, said ribs and/or cutouts 18 cooperating with the toothed block 11 of the sealing pin 3 for restricting a rotational movement of the sealing pin 3. The sealing pin 3 is axially displaceably arranged in a connector in accordance with the invention, preferably along the ribs and/or cutouts 18.

FIG. 6 shows a connector in accordance with the invention in the connected state, i.e. during the fluid supply through the connector. Fluid flows through the connector as illustrated by the arrow in FIG. 6. The sealing section 12 of the sealing pin 3 in this state is not in contact with the second connector part 2 so that fluid can flow.

Figure 7B:
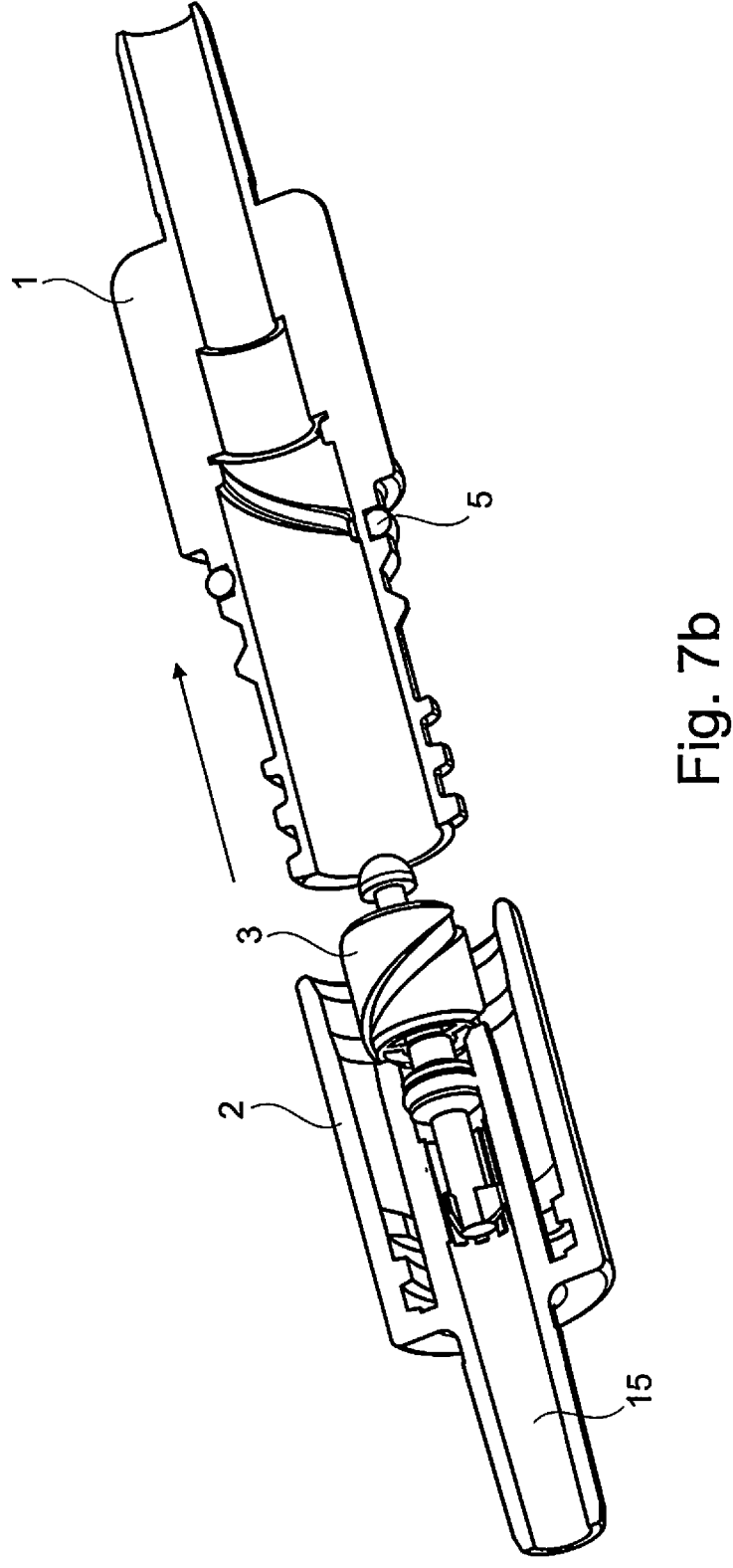

FIG. 7 explains the procedure of disconnection of a connector in accordance with the invention. The first connector part 1 is rotated in the direction of the arrow and is thereby unscrewed from the second connector part 2. Due to the threaded engagement between the sealing pin 3 and the first connector part 1, the sealing pin 3 also rotated until its rotation is restricted/stopped by an engagement of the toothed block 11 into the cutouts/ribs 18 of the second connector part. At the same time, the sealing pin 3, in particular its sealing section 12, is pressed into the lumen 15 of the second connector part 2 so that the lumen 15 is sealed in a fluid-tight manner by means of the O ring 5. The first connector part 1 is thereupon released from the second connector part 2, with the sealing pin remaining in/at the second connector part 2.

Provision can be made in a further embodiment that the sealing pin is projected over by the outer wall of the second connector part after the release of the two connector parts and thus represents a protection against contact.

Figure 8B:
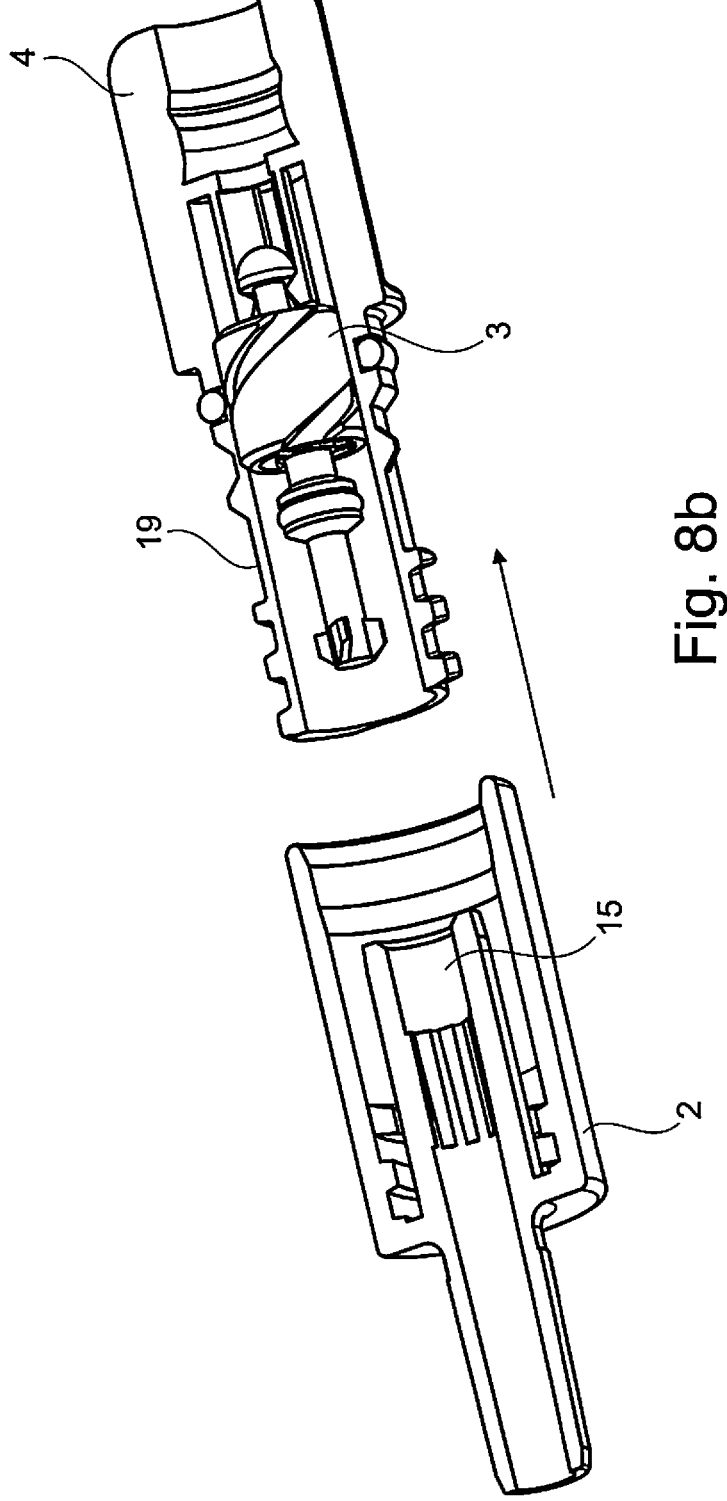

As shown in FIG. 8, a closure cap 4 can be place/screwed onto the first connector part 1, that preferably contains a disinfectant, after the disconnection. The closure cap has a corresponding threaded portion 19 for this purpose. The closure cap 4 in this embodiment has a receiver with a peripheral latching nose 20 in which the latching button 13 of the sealing pin is received when the closure cap 4 is applied to the second connector part 2 in the axial direction. The sealing pin is anchored at the closure cap 4 in this position. If the closure cap 4, including the sealing pin 3, is withdrawn from the second connector part 2, the lumen 15 of the second connector part is fluidically opened and is ready for a new connection.

In the above description, the use of the connector in accordance with the invention is illustrated with the reference to the example of a patient connection in peritoneal dialysis, for example. Shown schematically in FIG. 9, the connector in accordance with the invention can also be an element of a connection between an extracorporeal blood treatment apparatus 21, in particular a hemodialysis apparatus, and a disposable article 22 or can be an element of a connection between two disposable articles that can be used in hemodialysis. Disposable article has the meaning here of an article that is not provided to be permanently connected to the extracorporeal blood treatment apparatus, but is rather to be replaced after every treatment or after a plurality of treatments. Disposable articles in particular comprise all the articles that have a consumable that is used up during a treatment.

An advantage that can result from such a use comprises the sealing pin 3 first being able to serve as a flow-out protection, both for material 23, in particular fluids, and for solid elements such as powders or granulates, for the first connector part 1 and being able to serve as a flow-out protection for the second connector part 2 after the transfer to the second connector part 2. On a use of the cap 4, the outflow pin 3 can then be removed from the second connector part 2 again and the starting situation is reestablished, also with respect to the second connector part 2.

In an embodiment, the first connector part 1 can be an element of a disposable article 23 in the form of a concentrate container or can be connected thereto. The container can be a flexible bag or a container having a spatially fixed wall. A dry or liquid concentrate can be located in the bag. This concentrate can be or comprise sodium bicarbonate, for example. The first connector part 1 can be part of a connector component that provides two or more access ports to the interior of the bag, with the first connector part 1 forming a first access port of the access ports. "Port" here includes every direction, i.e. material can be transferred into and/or out of the container via this port. In further embodiments, two access ports or all the access ports can be formed in accordance with the first connector part 1. One or more or all of the connector parts 1 can each have a sealing pin. As can be seen from the above description, the connection of the first connector part 1 to the second connector part 2 can take place by means of a screwing movement. So that this is possible on provision of two first connector parts 1 that are directly or indirectly connected to one another, the first connector part 1 can be rotatably attached to the container. The first connector part 1 can thereby be freely rotatable relative to the container.

On the use of the concentrate container, it can be connected via the second connector part 2 to a fluid line of an extracorporeal blood treatment apparatus, in particular of a hemodialysis apparatus. The extracorporeal blood treatment apparatus has a port for this purpose that comprises the second connector part 2. Alternatively, the treatment apparatus can also have two or more ports that each comprise a second connector part 2. The second connector part 2 can be rotatably attached to the port. The second connector part 1 can thereby be freely rotatable relative to the port or to a body of the extracorporeal blood treatment apparatus. The second connector at the machine side can in particular be freely rotatable, whereas the first connector part 1 at the container side can be rigidly connected to the container. This can have the advantage that the disposable article can be manufactured less expensively and the second connector part 2 provided for reuse has a more complex design. In a further embodiment, the first connector part 1 is rotatable relative to the container and the second connector part 2 at the machine side is rigidly arranged in relation to the port.

To separate the connection, as shown schematically in FIG. 7, the extracorporeal blood treatment apparatus can have an automatic disconnection unit on whose activation the first connector part 1 and the second connector part 2 are separable in a rotational movement. The disconnection unit can have a motor and a fixing element, with the motor being configured as a drive to rotate the fixing unit and the fixing unit being configured to hold and rotate the first connector part 1 and/or the second connector part 2. Instead of a motor, a manual unit can also be provided that is adapted to transfer a force onto the fixing unit.

The same disconnection unit or a second disconnection unit can be provided in the blood treatment apparatus to separate the outflow pin 3 from the second connector part 3. The disconnection unit for the outflow pin 3 can be adapted to engage directly at the outflow pin 3 or via a disconnection aid, for example the cap 4 or another component that can be brought into engagement with the sealing pin 3. The second disconnection unit can, like the first disconnection unit, be automatically operable by a or the motor or can be manually operable.

In a further embodiment, the first connector part 1 is connected to a tube and the second connector part 2 is connected to a dialyzer or the second connector part 2 is connected to the tube and the first connector part 1 is connected to a dialyzer. It can thus be possible first to fill a dialyzer with fluid without the fluid escaping from the dialyzer via the first connector part, then to establish the connection to the tube, to likewise fill the latter, and to separate the dialyzer from the tube without fluid escaping from the tube via the second connector after completion of the treatment.

In a further embodiment, the first connector part 1 is connected to a tube and the second connector part 2 is connected to a port on the machine side.

The further embodiments can be combined or combinable in connection with an extracorporeal blood treatment apparatus that has one or more of the disconnection apparatus.

The extracorporeal blood treatment apparatus can have a connection apparatus or the disconnection apparatus can also be usable as a connection apparatus.

An advantage of the use of the connection systems in accordance with the invention can comprise the disposal article first being sealed by the sealing pin and no consumable being able to be lost, for example during transport. After the moving of the sealing pin to the port of the extracorporeal blood treatment apparatus, for example, a region connected thereto is produced that is accessible to further processes such as a disinfection with liquid disinfectants, without fluid being able to exit the treatment apparatus through the connector.

The invention claimed is:

1. A first connector part comprising:
   an elongate base body with a lumen for conducting a fluid;
   a first threaded portion that is arranged at an outer side of the base body and that enables a releasable connection of the first connector part to a correspondingly matched second connector part;
   a sealing pin that has a lumen arranged in the lumen of the elongate base body so that fluid is capable of flowing through and/or around the sealing pin and the lumen of the elongate base body; and
   a second threaded portion that is arranged at an inner side of the elongate base body at a lumen side and that enables a releasable connection of the first connector part to the sealing pin that is correspondingly matched to the second threaded portion, wherein
   the thread pitch of the first threaded portion differs from the thread pitch of the second threaded portion,
   the sealing pin furthermore has a bounding element that restricts a rotation of the sealing pin to one direction, and
   the sealing pin has a fixing element at the end opposite the bounding element, wherein the sealing pin is capable of being releasably or non-releasably fixed to a closure element via a latched connection and/or via an undercut.

2. The first connector part in accordance with claim 1, wherein, at its outer side, the sealing pin has a threaded portion that is adapted to enter into threaded engagement with the second threaded portion of the first connector.

3. A connector having the first connector part in accordance with claim 1 and having a second connector part, said connector comprising:

a receiving section of the second connector part concentrically surrounding the lumen of the elongate base body and for receiving the first threaded section arranged at the outer side of the elongate base body of the first connector part, wherein the receiving section of the second connector part has a threaded portion that is adapted to enter into threaded engagement with the first threaded portion of the first connector part and wherein the first connector part is releasably connected to the second connector part by means of a threaded engagement.

4. The connector in accordance with claim 3, wherein the sealing pin is arranged in a common lumen formed by the lumen of the first connector part and a lumen of the second connector part, with the sealing pin being movable by a relative movement of the first connector part to the second connector part between an open position in which the sealing pin blocks the fluid flow through the common lumen.

5. The first connector part in accordance with claim 1, wherein the first connector part is in total or in part an element of a connection between a blood treatment apparatus and a disposable article.

6. The first connector part in accordance with claim 1, wherein the first connector part is in fluid communication with a tube or in fluid communication with a dialyzer.

7. A method of fluidically connecting and/or disconnecting a medical connector, said method comprising the steps:

releasably connecting the first connector part in accordance with claim 1, to a second connector part, said medical connector having a receiving section of the second connector part concentrically surrounding the lumen of the elongate base body and for receiving the first threaded section arranged at the outer side of the elongate base body of the first connector part, wherein the receiving section of the second connector part has a threaded portion that is adapted to enter into threaded engagement with the first threaded portion of the first connector part, by screwing the first threaded portion of the first connector part to the threaded portion of the second connector part, with the first connector part having the sealing pin and a common lumen for conducting fluid being formed by the first connector part, by the second connector part, and by the lumen of the sealing pin;

releasing the first connector part from the second connector part by a rotational movement of the first connector part relative to the second connector part, whereby the sealing pin is moved into a closed position and remains in the second connector part when the first connector part is released from the second connector part; and releasably connecting a closure element, in the form of a closure cap, to the second connector part, whereby the sealing pin is pressed in the axial direction into the lumen of the second connector part, whereby the lumen of the second connector part is sealed to the outside in a fluid tight manner.

8. The method in accordance with claim 7, further comprising the step:

fixing the sealing pin to the closure element by means of the fixing element of the sealing pin that is fixed to a corresponding receiver of the closure element via the latching connection and/or via the undercut; and releasing the closure element from the connector part, wherein, at the same time as the release of the closure element, the sealing pin connected thereto is also released from the second connector part, whereby the lumen of the second connector part is fluidically opened.

9. A first connector part comprising:

an elongate base body with a lumen for conducting a fluid;

a first threaded portion that is arranged at an outer side of the base body and that enables a releasable connection of the first connector part to a correspondingly matched second connector part;

a sealing pin that has a lumen arranged in the lumen of the elongate base body so that fluid is capable of flowing through and/or around the sealing pin and the lumen of the elongate base body; and a second threaded portion that is arranged at an inner side of the base body at the lumen side and that enables a releasable connection of the first connector part to the sealing pin that is correspondingly matched to the second threaded portion, wherein the thread pitch of the first threaded portion differs from the thread pitch of the second threaded portion, and the sealing pin furthermore has a bounding element in the form of a toothed block, that restricts a rotation of the sealing pin to one direction.

* * * * *